United States Patent [19]

Alvarado

[11] Patent Number: 4,515,270
[45] Date of Patent: May 7, 1985

[54] SURGICAL GLOVE CARTON AND TRASH RECEPTACLE

[76] Inventor: Alfredo Alvarado, 1974 Heritage Rd., Huntingdon Valley, Pa. 19006

[21] Appl. No.: 589,827

[22] Filed: Mar. 15, 1984

[51] Int. Cl.³ .............................................. B65D 45/06
[52] U.S. Cl. .................... 206/438; 206/299; 229/87 A; 229/41 B
[58] Field of Search ........................ 206/438, 278, 299; 229/41 R, 41 B, 87 A, 87 J

[56] References Cited

U.S. PATENT DOCUMENTS

| | | | |
|---|---|---|---|
| 3,181,695 | 5/1965 | Taterka et al. | 206/299 |
| 3,187,987 | 6/1965 | Langdon | 229/87 A |
| 3,369,657 | 2/1968 | Quade et al. | 206/299 |
| 3,386,644 | 6/1968 | Zackheim | 229/41 B |
| 3,409,121 | 11/1968 | Taterka | 206/299 |
| 3,412,851 | 11/1968 | Coulombe | 206/299 |
| 3,746,152 | 7/1973 | Allen | 206/299 |
| 3,870,150 | 3/1975 | Hummel | 206/438 |
| 4,099,614 | 7/1978 | Heissenberger | 206/299 |
| 4,186,955 | 2/1980 | Campbell | 206/223 |
| 4,409,121 | 11/1968 | Taterka | 206/299 |

FOREIGN PATENT DOCUMENTS

| | | | |
|---|---|---|---|
| 369870 | 3/1932 | United Kingdom | 229/41 B |
| 1217574 | 12/1970 | United Kingdom | 229/41 R |
| 1533855 | 11/1978 | United Kingdom | 229/41 B |

*Primary Examiner*—William T. Dixson, Jr.
*Assistant Examiner*—Brenda J. Ehrhardt
*Attorney, Agent, or Firm*—Seidel, Gonda, Goldhammer

[57] ABSTRACT

A carton for containing a sterilized surgical glove pair is provided with four collapsible flaps. The flaps are raised by pulling on pull tabs. After the glove pair is removed, the flaps remain upright. The empty carton thus serves as a trash receptacle during the operating procedure.

4 Claims, 4 Drawing Figures

SURGICAL GLOVE CARTON AND TRASH RECEPTACLE

BACKGROUND OF THE INVENTION

This invention relates to a carton for packaging a pair of sterilized surgical gloves. Following removal of the gloves by the surgeon, the carton functions as a trash receptacle for receiving sponges, needles, etc. discarded during the surgical procedure.

During minor surgical procedures, a substantial quantity of soiled sponges and needles, expended syringes, suture materials, wrappers and other debris may be generated. These throw-away articles typically litter the operating tray surface hiding instruments from view, restricting the physician's access to instruments, and otherwise creating general confusion during the operating procedure. Such materials invariably find their way to the operating room floor, creating a slip-and-fall hazard to operating room personnel.

At least one discarded surgical glove carton is generally included in the operating room refuse. A single surgical glove pair may be packaged in a sterile book-like carboard carton, contained in an outer paper wrapper. The glove carton is generally formed of a stiff sheet material such as heavy gauge paper or cardboard, and provided with a series of fold lines for enclosing a single surgical glove pair. To gain access to the gloves, the outer wrapper is removed and the sterile carton is placed on the operating tray surface and unfolded to reveal left and right gloves. Such prior art surgical glove cartons are taught in U.S. Pat. Nos. 3,181,695; 3,369,657; 3,409,121; 3,412,851; 3,746,152; and 4,099,614. However, none of these cartons contain panels which are adapted for unfolding into a self-supporting upright position, thereby forming a four-sided box.

SUMMARY OF THE INVENTION

In accordance with the present invention, a collapsible carton for containing a pair of sterilized surgical gloves is provided. The carton includes a generally rectangular floor formed by a pair of opposing main body panels. The panels are joined by a center fold line bisecting the floor. Each main body panel restingly supports a surgical glove.

A pair of generally rectangular side flaps are foldably connected to opposite edges of the floor by fold lines perpendicular to the center fold line. The side flaps are bisected by a continuation of the center fold line. The side flaps are collapsable into the floor.

A pair of generally rectangular end flaps are foldably connected to opposite lateral edges of the body panels by end flap fold lines parallel to the center fold line. The end flaps are collapsible into the floor and the side flaps.

The end flaps and side flaps are foldably connected at their edges to form a four-sided collapsible enclosure around the floor. A diagonal side flap fold line extends across each side flap roughly 45° with respect to the floor from each one of the four corners of the floor.

The blank forming the present carton is easily stamped out from cardboard, heavy gauge paper, or like material.

It is an object of the present invention to provide a carton for a sterilized surgical glove pair which, when the glooves are removed, forms a four-sided enclosure which may serve as a trash receptacle on the operating tray surface.

Other objects and advantages are set forth hereinafter.

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
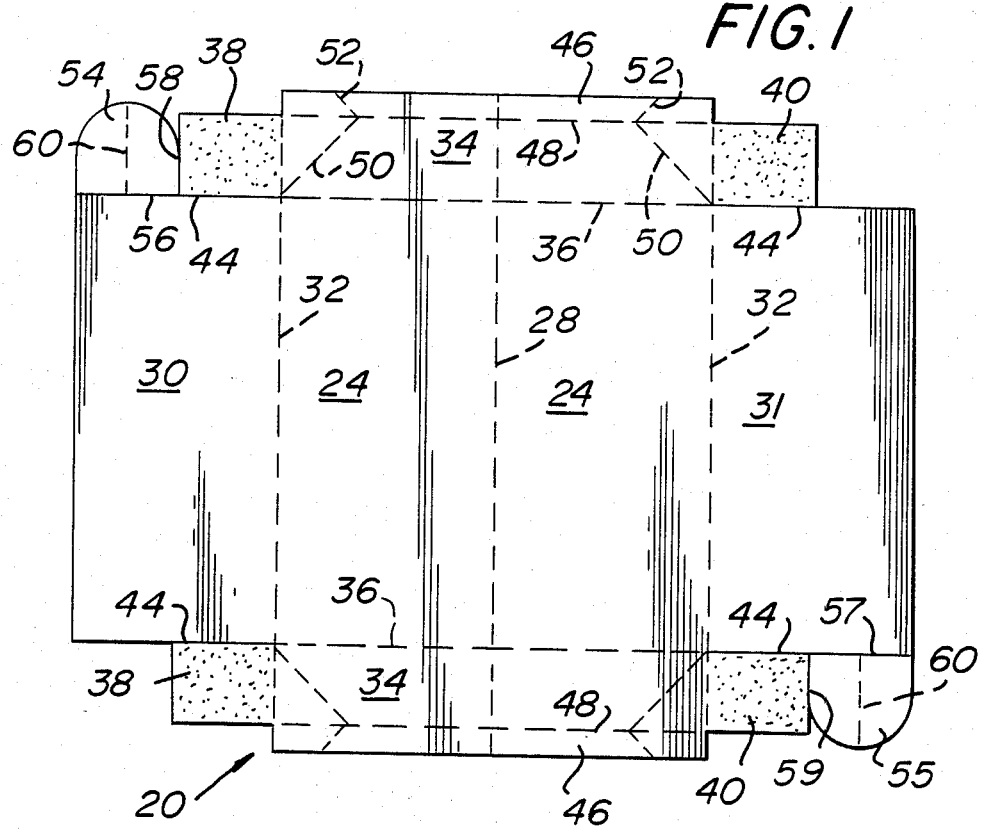
FIG. 1 is a top view of a blank shaped in accordance with the carton of the present invention.
Figure 2:
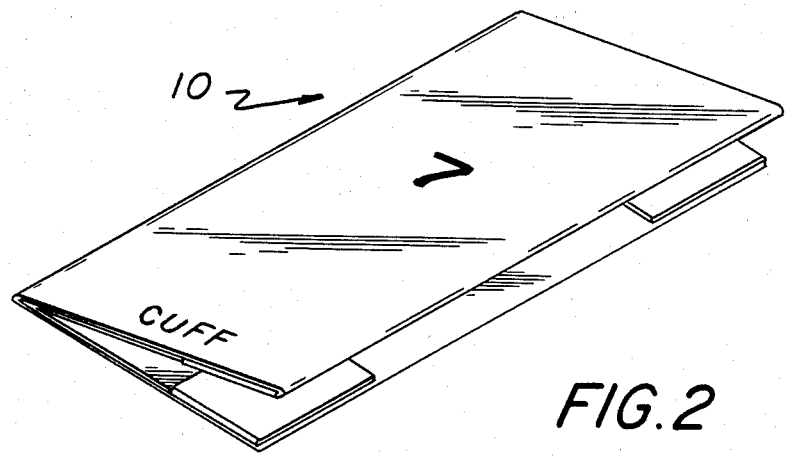
FIG. 2 is a perspective view of the collapsed carton, with main body panels folded over.

Referring to the drawings, the cut out and scored blank 20 of the carton generally designated as 10 is illustrated in FIG. 1. Blank 20 is formed of a sheet material, preferably heavy-weight paper of lightweight cardboard. The material used must be capable of withstanding standard sterilization.

The principal glove supporting portion consists of a generally rectangular floor 22 longitudinally bisected into opposing rectangular main body panels 24 by center fold line 28. Body panels 24 support a pair of surgical gloves 62 (shown in FIG. 4).

A pair of generally rectangular end flaps 30, 31 are foldably connected to opposite longitudinal edges of body panels 24 by end flap fold lines 32 which run parallel to center fold line 28.

A pair of generally rectangular side flaps 34 are foldably connected to opposite lateral edges of floor 22 by side flap fold lines 36. Side flap fold lines 36 run perpendicular to center fold line 28. Side flaps 34 are laterally bisected by a continuation of center fold 28. A diagonal side flap fold line 50 extends across each side flap 34 at an angle of approximately 45° with respect to the floor from each one of the floor corners of the floor terminating at cuff fold line 48.

A generally rectangular cuff 46 is foldably connected to the lateral edge of each side flap 34 by mean of a cuff fold line 48 which runs parallel to side flap fold lines 36. Cuffs 46 are laterally bisected by an extension of center fold line 28.

A diagonal cuff fold line 52 extends from each point of intersection of side flap diagonal fold lines 50 with cuff fold lines 48 across cuff 46, thereby describing an included angle of approximately 90° with side flap diagonal fold lines 50. When the assembled carton is in collapsed configuration, cuff 46 is folded against side flap 34, and each diagonal cuff fold line is superimposed on its associated side flap diagonal fold line.

A pair of wings 38 lie adjacent end flap 30. Likewise, a pair of wings 40 lie adjacent end flap 31. Each wing is formed by a roughly rectangular extension of side flaps 34. Each wing is foldably connected to a side flap 34 by an extension of end flap fold lines 32. Each wing is separated from an associated end flap 30 or 31 by wing cut lines 44.

Generally simicircular-shaped tabs 54, 55 are stamped out with stamping of the main body of blank 20. Tab 54 lies along a lateral edge of end flap 30, and borders wing 38. Tab 54 is separated from end flap 30 and wing 38 by cut lines 56 and 58, respectively. Diagonally opposite floor 22, tab 55 is likewise separated from end flap 31 and wing 40 by cut lines 57 and 59, respectively. Tab fold lines 60, 61 bisect tabs 54, 55 respectively along their longitudinal axes.

Figure 4:
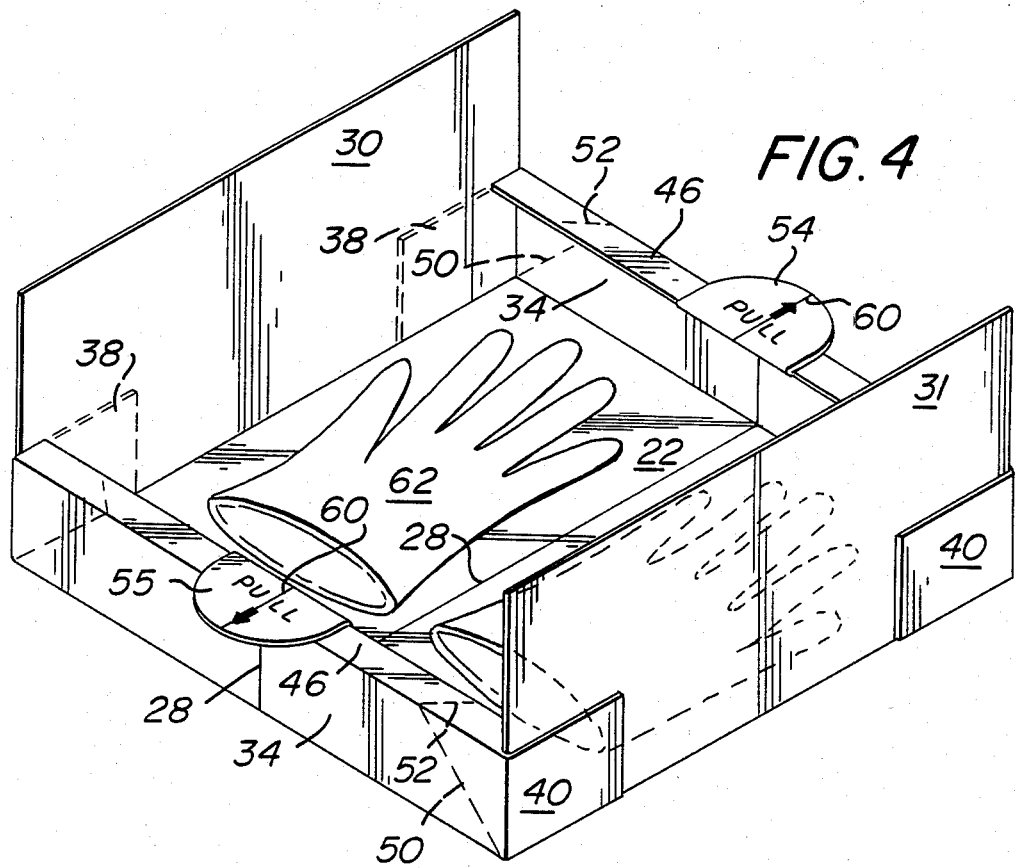
FIG. 4 is a view similar to FIG. 3, but showing the carton with flaps raised.

Blank 20 is stamped out with tabs 54 and 55 being stamped out at the same time. Blank 20 is assembled into carton 10 in the following manner. Tabs 54, 55 are attached to respective cuffs 46 by adhesive means to point outwardly from blank 20. Tabs 54, 55 are affixed in such a manner such that tab fold lines 60 line up with center fold line 28, as shown in FIG. 4.

End flaps 30, 31 are first raised to a position perpendicular to floor 22. Side flaps 34 are raised in a similar fashion, and cuffs 46 are folded over 90° such that they lie in a plane parallel to floor 22. Wings 38, to which adhesive has been applied, are folded inwardly to contact and become affixed to the outer surface of end flap 30. Wings 40 are similarly affixed to end flap 31. Tabs 54, 55 affixed to opposite side flap cuffs 34 are disposed outwardly in a plane parallel to carton floor 22 to permit grasping by the surgeon. The assembled carton is shown in FIG. 4.

Figure 3:
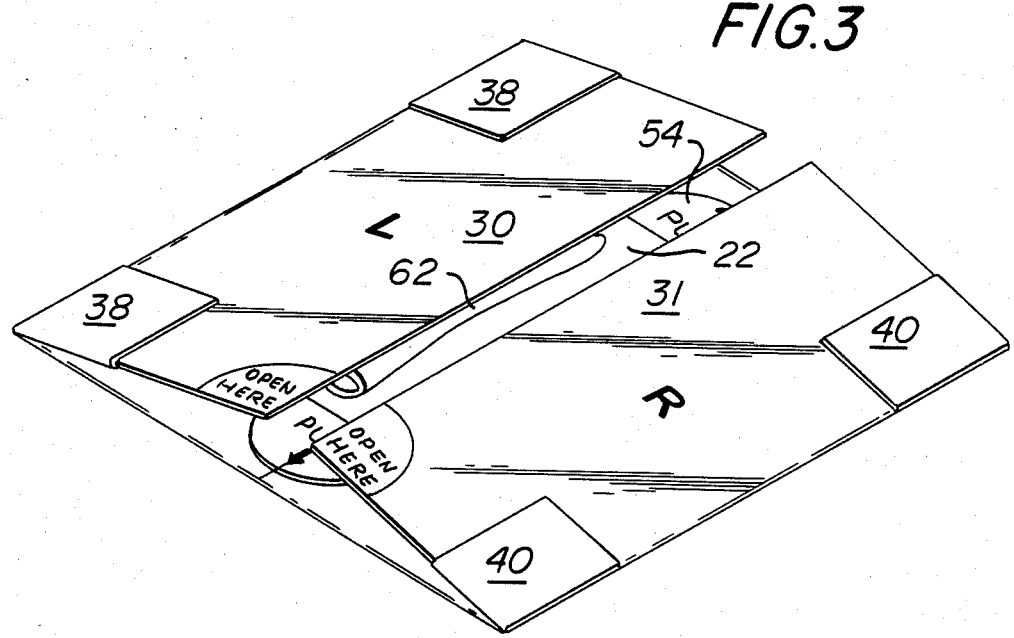
FIG. 3 is a perspective view of the collapsed carton, with main body panels unfolded.

Side flaps 34 are collapsible into floor 22 by virtue of a pair of diagonal fold lines 50 in each side flap 34 and diagonal fold lines 52 in cuffs 46. The collapsed carton with side flaps and end flaps collapsed into the floor is shown in FIG. 3. The carton is erected by pulling on the pull tabs in opposing directions which causes the side flaps 34 and end flaps 30 of the carton to to be raised to the configuration shown in FIG. 4.

After the gloves are removed, the carton remains erected to serve as a trash receptacle for refuse generated during the operating procedure.

The present invention may be embodied in other specific forms without departing from the spirt or essential attributes thereof and, accordingly, reference should be made to the appended claims, rather than to the foregoing specification, as indicating the scope of the invention.

I claim:

1. A collapsible carton for containing a pair of sterilized surgical gloves comprising:

(a) a generally rectangular floor, said floor being formed by a pair of opposing main body panels joined by a center fold line bisecting said floor, each main body panel restingly supporting a surgical glove;
   (b) a pair of generally rectangular side flaps foldably connected to opposite edges of the floor by side flap fold lines perpendicular to said center fold line, said side flaps bisected by a continuation of the center fold line and being collapsible into the floor;
   (c) a pair of generally rectangular end flaps foldably connected to opposite lateral edges of the body panels by end flap fold lines parallel to the center fold line, said end flaps being collapsible into the floor and said side flaps, said end flaps and side flaps being foldably connected at their edges to form a four-sided collapsible enclosure around said floor;
   (d) a generally rectangular cuff foldably connected to the lateral edge of each side flap, said cuff being bisected by an extension of the center fold line and folded over 90° such that it lies in a plane parallel to the carton floor; and
   (e) a pull tab affixed by adhesive means to each cuff for grasping, said pull tab being disposed outwardly from the carton in a plane parallel to the floor.

2. A collapsible carton in accordance with claim 1 wherein a side flap diagonal fold line extends across each side flap roughly 45° with respect to the floor from each one of four corners of the floor.

3. A collapsible carton in accordance with claim 2 wherein a diagonal cuff fold line extends diagonally across each cuff from a point of intersection of said side flap diagonal fold line and a fold line forming the boundary between said cuff and its associated side flap, said diagonal cuff fold line describing an included angle of approximately 90° with said side flap diagonal fold line.

4. A collapsible carton in accordance with claim 2 wherein said pull tabs are bisected by longitudinal fold lines.

* * * * *